US009606060B2

United States Patent
Chen et al.

(10) Patent No.: US 9,606,060 B2
(45) Date of Patent: Mar. 28, 2017

(54) FILTERLESS TIME-DOMAIN DETECTION OF ONE OR MORE FLUOROPHORES

(71) Applicant: CALIFORNIA INSTITUTE OF TECHNOLOGY, Pasadena, CA (US)

(72) Inventors: Samson Chen, Flushing, NY (US); Aditya Rajagopal, Irvine, CA (US); Axel Scherer, Barnard, VT (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 942 days.

(21) Appl. No.: 13/740,112

(22) Filed: Jan. 11, 2013

(65) Prior Publication Data
US 2013/0183676 A1    Jul. 18, 2013

Related U.S. Application Data (60) Provisional application No. 61/586,577, filed on Jan. 13, 2012.

(51) Int. Cl.
G01N 21/64       (2006.01)
(52) U.S. Cl.
CPC ..... G01N 21/6486 (2013.01); G01N 21/6408 (2013.01)
(58) Field of Classification Search
CPC ................. G01N 21/6408; G01N 21/6486
See application file for complete search history.

(56) References Cited

U.S. PATENT DOCUMENTS 5,784,157 A    7/1998   Gorfinkel et al.
6,447,724 B1   9/2002   Jensen et al.

OTHER PUBLICATIONS

A Novel Filterless Fluorescence Detection Sensor for DNA Analysis, Maruyama et al., IEEE Transactions on Electron Devices, vol. 53, No. 3, Mar. 2006.*
The fabrication of filter-less fluorescence detection sensor array using CMOS image sensor technique, Maruyama et al., Sensors and Actuators A 128 (2006) 66-70.*
Full spectrum filterless fluorescence microscopy, Booth et al., Journal of Microscopy, 2009, Received May 29, 2009; accepted Jul. 21, 2009.*
Handbook of Optical Filters for Fluorescence Microscopy, Reichman, Jun. 1998.*
Optical filtering technologies for integrated fluorescence sensors, Dandin et al., First published as an Advance Article on the web Jul. 10, 2007.*
Jobin Yvon Horiba Group, Which Fluorescence Lifetime System is Best for You? 2004, 4 pages total.

* cited by examiner

*Primary Examiner* — Shogo Sasaki
(74) *Attorney, Agent, or Firm* — Steinfl + Bruno LLP (57) ABSTRACT

A device and method are described in which the lifetime of a fluorescent species or fluorophores is detected in the absence of any optical filter. Based on the measured fluorescent lifetimes, molecules or compounds attached to a fluorophores such as small organic molecules, polymers, peptides, saccharides and nucleic acids can be identified or assayed.

18 Claims, 8 Drawing Sheets

FILTERLESS TIME-DOMAIN DETECTION OF ONE OR MORE FLUOROPHORES

CROSS REFERENCE TO RELATED APPLICATIONS

The present application claims priority to U.S. Provisional Application No. 61/586,577, entitled "Time-domain multiplex detection of fluorescent DNA sequence probes" filed on Jan. 13, 2012, which is incorporated herein by reference in its entirety.

FIELD

The present disclosure relates to detection of fluorescents. In particular, it relates to filterless time-domain detection of one or more fluorophores.

BACKGROUND

In numerous fields, including organic chemistry and molecular biology, there is a growing need for efficient and cost-effective methods to perform fluorescent detection. The optics required to differentiate several fluorescent wavelengths and the excitation wavelength while simultaneously illuminating a sample with light is often complex and expensive. Developing devices that utilize the characteristic decay time of fluorophores instead of emission spectra can provide a cost-effective alternative to heavier and larger form factors involving optical filters.

SUMMARY

According to a first aspect of the disclosure, a detection circuit for fluorescent species is described, the detection circuit comprising a fluorescent chemical species excitation arrangement; a filterless fluorescent chemical species detection arrangement; a control circuit configured to independently enable or disable the fluorescent species excitation arrangement and the fluorescent species detection arrangement; and a signal processing circuit, operatively connected with the fluorescent chemical species detection arrangement and configured to generate time varying characteristics as a function of the output of the fluorescent species detection arrangement, the time varying characteristics being indicative of the fluorescent species.

According to the second aspect of the disclosure, a method for detecting fluorescent species, the method comprising exciting a fluorescent species during an excitation time window where excitation in absence of detection occurs, the fluorescent species emitting a species-indicative light intensity level upon excitation; detecting the species-indicative light intensity level during a detection time window where detection in absence of excitation occurs, thus providing a species-indicative time varying detection signal; processing the species-indicative time varying detection signal; generating a species-indicative measurement data based on the processing; repeating the exciting, detecting, processing, and generating, accumulating the species-indicative measurement data obtained after the repeating; and deriving a accumulated species-indicative data based on the accumulating.

The details of one or more embodiments of the disclosure are set forth in the accompanying drawings and the description below. Other features will be apparent from the description and drawings, and from the claims

BRIEF DESCRIPTION OF DRAWINGS

The accompanying drawings, which are incorporated into and constitute a part of this specification, illustrate one or more embodiments of the present disclosure and, together with the detailed description and examples sections, serve to explain the principles and implementations of the disclosure.

DETAILED DESCRIPTION

The term "filterless" as used herein indicates the absence of wavelength-dependent optical filters.

The term "sample" as used herein indicates a limited quantity of something that is indicative of a larger quantity of that something, including but not limited to solids and/or fluids from a biological environment, specimen, cultures, tissues, commercial recombinant proteins, synthetic compounds or portions thereof.

The terms "fluorescent" or "fluorescence" as used herein indicates the emission of light by a substance that has absorbed light or other electromagnetic radiation and during the excitation period, some of the energy is dissipated by molecular collisions or transferred to a proximal molecule, and then the remaining energy is emitted as a photon to relax the electron back to the ground state. The emitted light can have a longer wavelength than the absorbed light, a shorter wavelength than the absorbed light, or the same wavelength as the absorbed light. In many cases, the emitted photon carries less energy and therefore has a longer wavelength than the excitation photon, and thus the emitted fluorescence can be distinguished from the excitation light. The excitation and photon emission from a fluorophore is cyclical until the fluorophore is irreversibly damaged.

The term "fluorophore" or "fluorochrome" or "fluorescent species" as used herein indicates substance which itself fluoresces or can be made to fluoresce. Each term is interchangeable. Fluorophores can be used alone or covalently attached to another molecule. The process of covalently attaching a fluorophore to another molecule or compound is referred to as "fluorescent labeling". Exemplary fluorophores include but are not limited to those listed in Table 1.

TABLE 1

Fluorophore Table

| Dye | Absorbance Wavelength | Emission Wavelength | Visible color |
|---|---|---|---|
| Hydroxycoumarin | 325 | 386 | blue |
| methoxycoumarin | 360 | 410 | blue |
| Alexa fluor | 345 | 442 | blue |
| aminocoumarin | 350 | 445 | blue |
| Cy2 | 490 | 510 | green (dark) |
| FAM | 495 | 516 | green (dark) |
| Alexa fluor 488 | 494 | 517 | green (light) |
| Fluorescein FITC | 495 | 518 | green (light) |
| Alexa fluor 430 | 430 | 545 | green (light) |
| Alexa fluor 532 | 530 | 555 | green (light) |
| HEX | 535 | 556 | green (light) |
| Cy3 | 550 | 570 | yellow |
| TRITC | 547 | 572 | yellow |
| Alexa fluor 546 | 556 | 573 | yellow |
| Alexa fluor 555 | 556 | 573 | yellow |
| R-phycoerythrin (PE) | 480; 565 | 578 | yellow |
| Rhodamine Red-X | 560 | 580 | orange |
| Tamara | 565 | 580 | red |
| Cy3.5 581 | 581 | 596 | red |
| Rox | 575 | 602 | red |
| Alexa fluor 568 | 578 | 603 | red |
| Red 613 | 480; 565 | 613 | red |
| Texas Red | 615 | 615 | red |
| Alexa fluor 594 | 590 | 617 | red |
| Alexa fluor 633 | 621 | 639 | red |
| Allophycocyanin | 650 | 660 | red |
| Alexa fluor 633 | 650 | 668 | red |
| Cy5 | 650 | 670 | red |
| Alexa fluor 660 | 663 | 690 | red |
| Cy5.5 | 675 | 694 | red |
| TruRed | 490; 675 | 695 | red |
| Alexa fluor 680 | 679 | 702 | red |
| Cy7 | 743 | 770 | red |
| DAPI | 345 | 455 | blue |
| Hoechst 33258 | 345 | 478 | blue |
| SYTOX blue | 431 | 480 | blue |
| Hoechst 33342 | 343 | 483 | blue |
| YOYO-1 | 509 | 509 | green |
| SYTOX green | 504 | 533 | green |
| TOTO1, TO-PRO-1 | 509 | 533 | green |
| SYTOX orange | 547 | 570 | yellow |
| Chromomycin A3 | 445 | 575 | yellow |
| Mithramycin | 445 | 575 | yellow |
| Propidium iodide | 536 | 617 | red |
| Ethidium bromide | 493 | 620 | red |

A molecule or compound that can be labeled with fluorophores include but are not limited to an organic molecule, an amino acid, a peptide, a polypeptide, a protein, a nucleotide, a nucleoside, a dideoxynucleoside, a dideoxynucleotide, a deoxynucleoside, a deoxynucleotide, a nucleotide analog, a nucleoside analog, a polynucleotide, a nucleic acid, a sequencing reaction product, a PCR reagent, a nucleic acid template, a nucleic acid primer, an antibody, an antigen, a ligand, a receptor, an enzyme, an enzyme substrate, a monomer, a polymer, a drug, a sugar, a polysaccharide, a lipid, a liposome, a micelle, a toxin, or a cell. A molecule or compound can be labeled by more than one fluorophore or fluorescent species.

The term "multiplex detection" as used herein indicates detection and/or quantification of multiple analytes in a sample or multiple samples.

The term "fluorescence lifetime" as used herein indicates the average time the molecule stays in its excited state between being excited by a photon and subsequently emitting a photon. The statistical distribution of the fluorescence lifetime is Poisson-distributed and results in an exponential decay when a population of fluorophores, previously excited by a light source, ceases to receive any new excitation, as described by Equation 1.

$$F(t) = F_0 e^{-t/\tau} \qquad \text{Equation 1}$$

Figure 1:
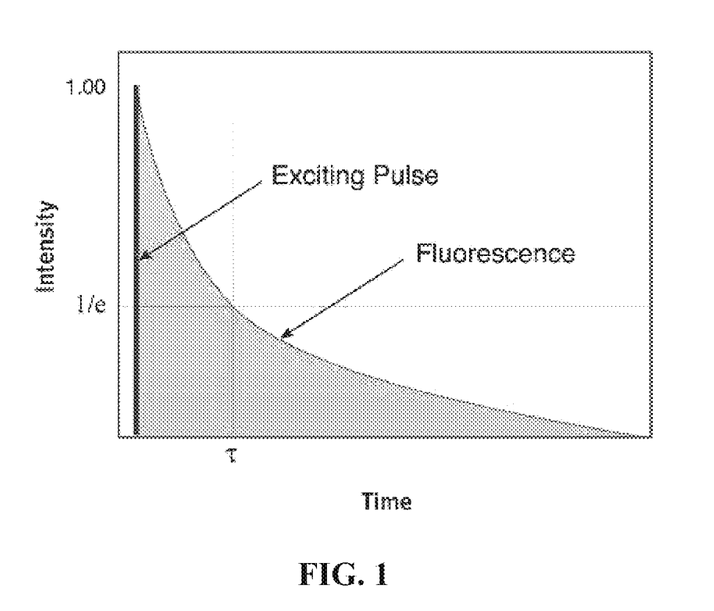
FIG. 1 shows a plot of fluorescence intensity as a function of time, F(t).

In Equation 1, t is time, F(t) is the fluorescence light intensity at time t, $\tau$ is the fluorescence lifetime (equal to the average time a single molecule stays in its excited state, as derived from the statistics of a Poisson distribution), and $F_0$ is the initial fluorescence light intensity at t=0. More importantly, the lifetime, $\tau$, is independent of the initial intensity of the emitted light. The fluorescence intensity as a function of time, F(t), thus gradually decays to near zero after several times the fluorescence lifetime T. For example, at t=$\tau$, the fluorescence has decayed to ~37%, at t=2$\tau$, to 14%, at t=3$\tau$, 5%, and so forth. A plot of the fluorescent decay can be found in FIG. 1. Exemplary fluorophores lifetimes with excitation and emission maximum values, but not limited to, are listed in Table 2.

TABLE 2

Commonly used fluorophores and their fluorescence lifetimes.

| Fluorophore | Lifetime [ns] | Excitation Max [nm] | Emission Max [nm] |
|---|---|---|---|
| ATTO 655 | 3.6 | 655 | 690 |
| Acridine Orange | 2 | 500 | 530 |
| Alexa Fluor 488 | 4.1 | 494 | 519 |
| Alexa Fluor 647 | 1 | 651 | 672 |
| BODIPY FL | 5.7 | 502 | 510 |
| Coumarin 6 | 2.5 | 460 | 505 |
| CY3B | 2.8 | 558 | 572 |
| CY3 | 0.3 | 548 | 562 |
| CY5 | 1 | 646 | 664 |
| Fluorescein | 4 | 495 | 517 |
| Oregon Green 488 | 4.1 | 493 | 520 |
| Ru(bpy)$_2$(dcpby)[PF$_6$]$_2$ | 375 | 458 | 650 |
| Pyrene | >100 | 341 | 376 |
| Indocyanine Green | 0.52 | 780 | 820 |
| Rhodamine B | 1.68 | 562 | 583 |
| Lanthanide-based dyes | microseconds to milliseconds | various | various |

Figure 2:
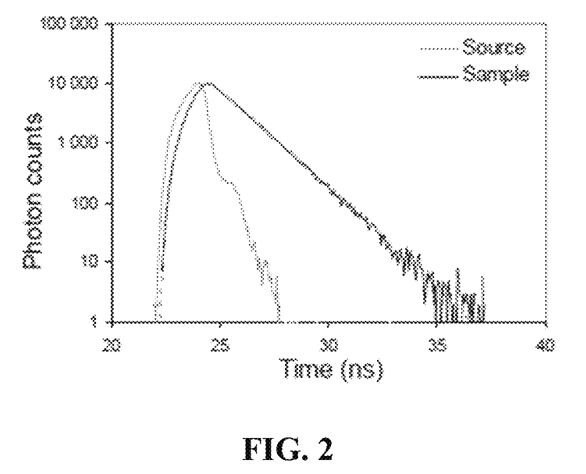
FIG. 2 shows the gradual decay of fluorescence intensity or photocounts with time with a pulsed light-source (gray) and sample response (black).
Figure 3:
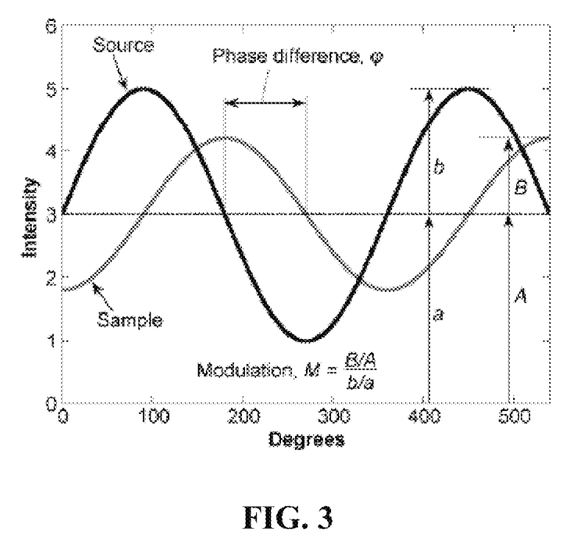
FIG. 3 shows the excitation (black) and sample response (gray), illustrating the phase-angle shift ($\phi$) and demodulation ratio (M) used in frequency domain methods.

Fluorescence lifetimes are often measured using the "time domain" method or the "frequency domain" method. The term "time domain" method as used herein indicates illuminating a sample with a fluorophore with a short pulse of light and the intensity of the emission versus time is recorded to determine fluorescence lifetime (see FIG. 2). The term "frequency domain method" as used herein indicates exciting a sample with a fluorophore by a modulated source of light and calculating the modulation (M) and phase-shift ($\phi$) of the emitted light to determine fluorescence lifetime (see FIG. 3).

The lifetime of any fluorescent species can be detected by either method. A major difference between time domain and frequency domain methods is that the latter requires the generation of an extremely low distortion continuous wave and expensive very high speed analog circuitry to amplify, measure, and analyze the data, whereas the former only requires that a population of fluorophores is excited any light source capable of turning off quickly or providing pulses of light. As a result, instruments utilizing the time domain method are compatible with precise and inexpensive light sources such as light-emitting diodes and pulsed diode-laser sources.

Devices to detect fluorescence lifetimes that utilize time domain analysis often require filtering elements to avoid an overlap of excitation source spectra and detectable fluorescence emission spectra. The embodiments herein describe a filterless time-domain device to perform multiplex detection of fluorophores or fluorescent species. Instead of using optics to differentiate signals, electronic time measurement and signal analysis circuitry, which is typically less expensive, simpler, and more compact, is used.

Figure 4:
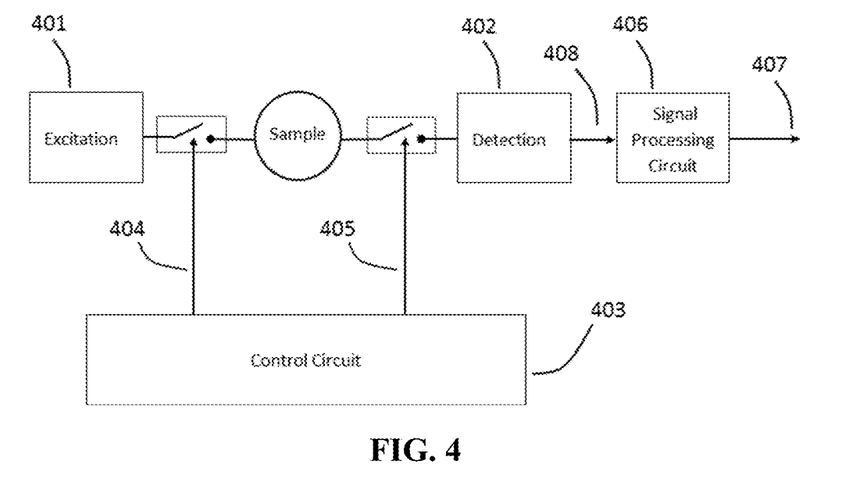
FIG. 4 illustrates an exemplary block diagram of a basic circuit to implement filterless time-domain detection of a fluorescent species.

The block circuit diagram of FIG. 4 is an exemplary embodiment of a filterless time-domain multiplex detector for fluorophores. FIG. 4 shows a fluorescent chemical species excitation arrangement (401), a fluorescent chemical species detection arrangement (402), a filterless control circuit (403) configured to independently enable or disable (404, 405) the fluorescent species excitation arrangement (401) and the fluorescent species detection arrangement (402). In addition, FIG. 4 shows a signal processing circuit (406) which is operatively connected with the fluorescent chemical compound detection arrangement (402) and configured to generate a time varying characteristics (407) as a function of the output (408) of the fluorescent species detection arrangement (402). In this embodiment, the time varying characteristics are indicative of the fluorescent species within a sample, along with their concentrations within a sample.

Figure 5A:
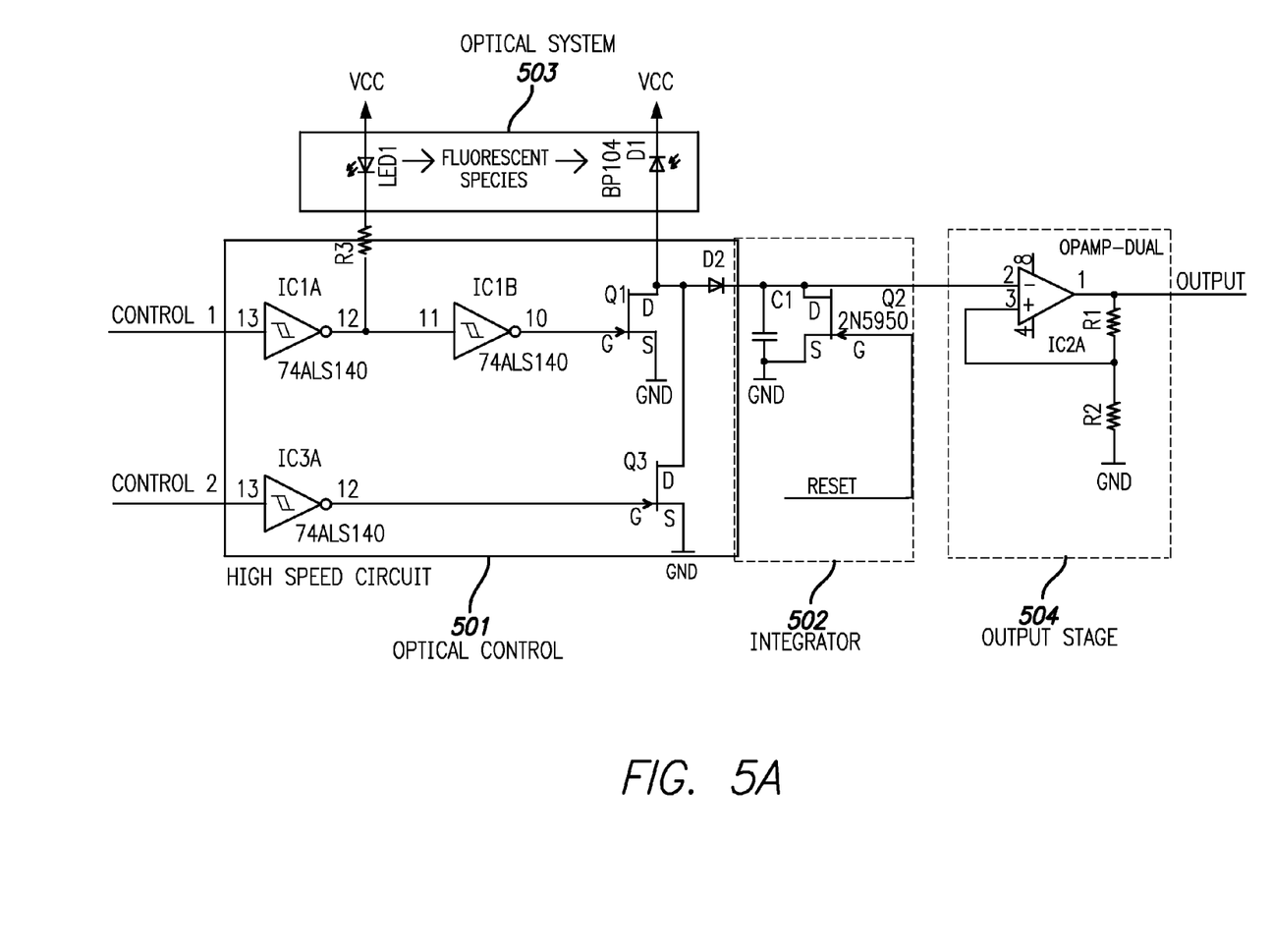
FIGS. 5A and 5B show an exemplary circuit and block diagram of a filterless time-domain detector for fluorophores illustrated in FIG. 4.
Figure 5B:
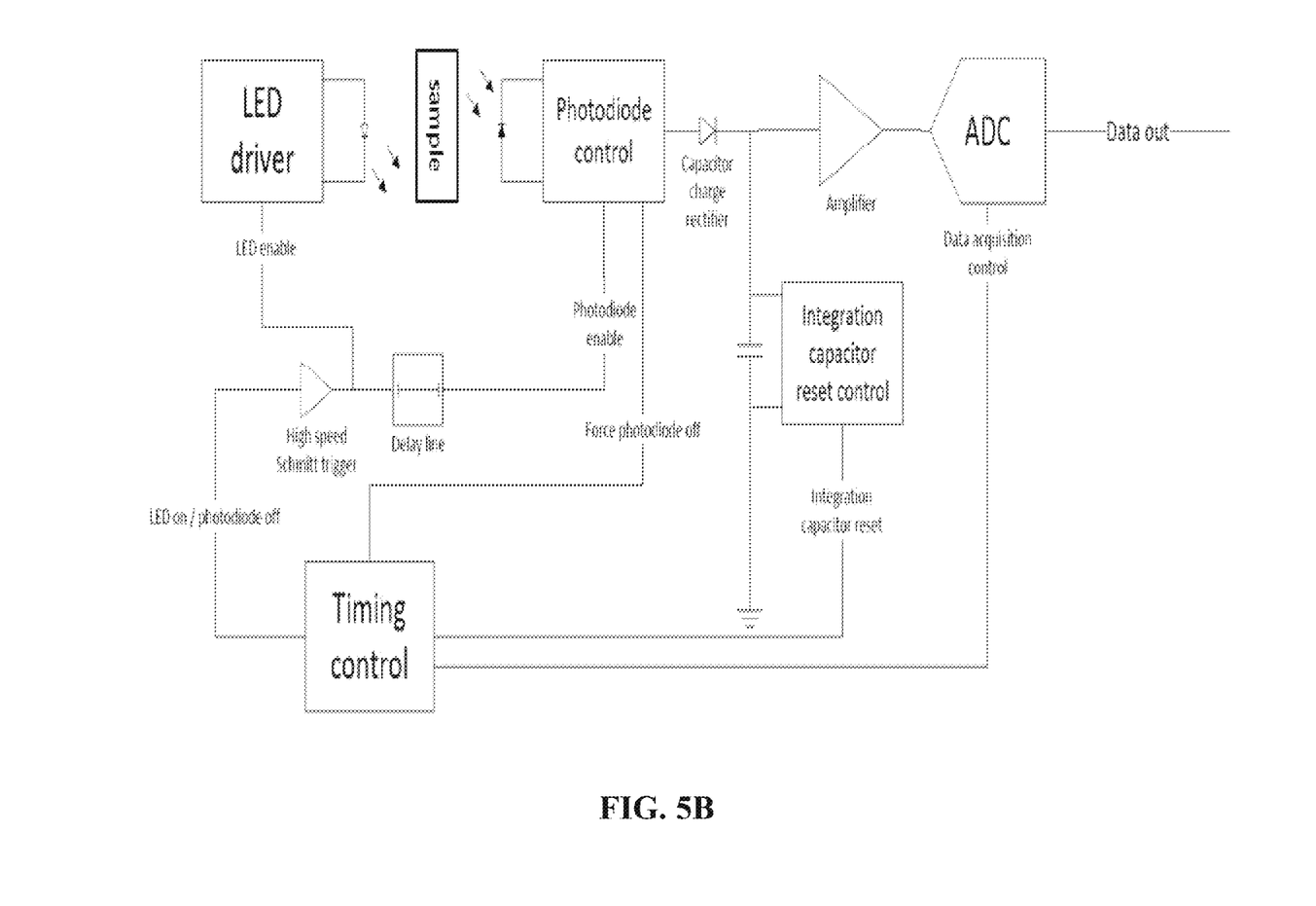

FIGS. 5A and 5B shows an exemplary circuit of a filterless time-domain detector of at least one fluorophores illustrated in FIG. 4. In the embodiment of FIG. 5A, the circuit comprises four modules: A high speed optical control module (501), an integrator (502), an optical system (503) and an output stage (504). The fluorescent species to be measured is placed within the optical system (503) which is devoid of any optical filter. The optical control module (501) interacts with the optical system (503) to enable/disable various optical measurement related phases (e.g. excitement, detection). The integrator (502) generates a voltage corresponding to the characteristic of the fluorescent species. The output stage (504) amplifies and drives the voltage generated by the integrator (502) to the outside world for measurement and further processing, if necessary. FIG. 5B provides a block diagram of the same.

More in particular, the optical system (503) contains a fluorescent species which is excited by a wavelength ($\lambda 1$) emitted by light-emitting diode (LED1) and in response to which wavelength it emits a wavelength ($\lambda 2$) which, in turn, is detected by the photodetector D1. Biasing for both LED1 and D1 is provided by the supply voltage Vcc.

The optical control module (501) controls operation of both LED1 and D1 via two independently controlled signals CONTROL1 and CONTROL2. When CONTROL1 is in the high state (e.g. 5 V), the output of the 74ALS series Schmitt-trigger inverter (IC1A) is low, which enables current to flow through LED1 (as regulated by resistor R3), causing LED1 to turn on and emit light. At the same time, when CONTROL1 is in the high state, the output of the 74ALS series Schmitt-trigger inverter (IC1B) is high, which turns on the high speed metal-oxide-semiconductor field-effect (MOSFET) transistor Q1 and thus shorting the photodetector to ground (since VDS~0 V), which in turn routes all the current flowing through the photodetector, which is proportional to the light intensity detected by the photodetector D1 (photocurrent), to ground.

When CONTROL1 is in the low state, LED1 is disabled and transistor Q1 is turned off, causing the current flowing through the photodetector (D1) to be routed to the integrator module (502). When CONTROL2 is in the low state (e.g. 0 V), output of the Schmitt-trigger inverter IC3A is high, which also turns on the high speed MOSFET Q3 and thus allows current proportional to the light intensity detected by the photodetector (D1) to flow through ground and not being routed to the integrator module (502). It is to be noted that CONTROL1 enables/disables the detector D1 and disables/enables photocurrent to the integrator module concurrently, whereas CONTROL2 only enables/disables the detector D1, independent of the state of the LED1.

The integrator (502) comprises a charging capacitor C1, which charges in response to a current flowing through the diode D2, and discharges in response to a RESET control signal. When the RESET control signal is in the high state, the junction gate field-effect transistor (JFET) Q2 is enabled thus fast discharging the charge accumulated across the capacitor C1, and thus causing the voltage across capacitor C1 to drop to a near zero voltage (0 V). When RESET is in the low state, Q2 is not conducting and is electrically equivalent to a high impedance device. This allows the capacitor C1 to charge as a function of the current flowing through D2. If there is no current flowing through D2 or if this current is shunted to ground (e.g. Q1 or Q3 turned on), the capacitor does not charge and will maintain substantially the same voltage across it for a certain amount of time, as such voltage will decay in a very slow fashion and as a function of the high impedance created by the transistor Q2 and the input of the circuitry around the operational amplifier IC2A.

The exemplary output stage (504) shown in FIG. 5A comprises an OpAmp (IC2A) amplifier configured as non-inverting amplifier with a gain determined by the two resistors R1 and R2. The non-inverting configuration is chosen due to its very high input impedance and thus minimum load presented to the charging capacitor C1.

The exemplary circuit shown in FIG. 5A can be used to implement filterless time-domain detection of fluorescent species. In particular, such circuit is capable of synchronizing the excitation light source (e.g. emitted by LED1) and the light detection circuit so that detection (e.g. via detector D1) only occurs immediately after the excitation light source is turned off and within the lifetime of the fluorescent species.

The embodiment of FIG. 5A allows for a filterless time-domain detection scheme with a relatively low cost design despite the fast detection cycles which may be required (depending, e.g., on the lifetime of the fluorophore). Only a single part of the detection scheme shown in FIG. 1 should be fast—the transition between the two states (one state being excitation light source on, detector circuit off; the other state being excitation light source off, detector circuit on). Thus, the high frequency portion of the circuit can be limited to few components surrounding the light source (LED1) and light sensor (D1) and be primarily designed with off-the-shelf, low cost high speed logic gates and transistors.

The circuit of FIG. 5A operates in accordance with four states, controlled by the logic signals CTRL1 (for CONTROL1), CTRL2 (for CONTROL2), and RES (for RESET), where, as usual, 0 is used to represent a low logic value and 1 is used to represent a high logic value:

State 1: Emission source off, detection circuit off, integration capacitor reset on (CTRL1=0, CTRL2=1, RES=1)

State 2: Emission source on, detection circuit off, integration capacitor reset off (CTRL1=1, CTRL2=0, RES=0)

State 3: Emission source off, detection circuit on, integration capacitor reset off (CTRL1=0, CTRL2=0, RES=0)

State 4: Emission source off, detection circuit off, integration capacitor reset off (CTRL1=0, CTRL2=1, RES=0)

State 1 occurs at the beginning of any new measurement, and clears an old value in the circuit from the previous measurement. This value represents a charge accumulated across the capacitor C1 and which can be reset to zero via the RESET signal.

After clearing the old value and to begin a measurement, the circuit proceeds to State 2, where the excitation source (LED1) is turned on and the detection circuit (D1, Q1, Q3) is left off. The fluorescent species is now receiving light from the excitation source, and shortly begins to emit light (fluoresce).

After sufficient time (e.g., at least several times the fluorescent lifetime of the species), the amount of light emitted from the fluorescent species becomes relatively constant. The excitation source is now turned off, bringing the circuit into State 3. After a short delay caused by physical limitations of the excitation source and by the time taken by light to travel, the fluorescent species stops receiving excitation light and the amount of fluoresced light begins to decay. After a built-in delay, which can be timed to the instant when the light sensor ceases to receive any light directly originating from the excitation light source, the photocurrent output of the light sensor (D1) is rerouted to an integration capacitor (C1). The voltage across the capacitor (C1) thus becomes proportional to the amount of light emitted by the fluorescent species over time, which is consequently equivalent to the amount of the fluorescent species present. It should be noted that beyond the fluorescent lifetime of the fluorescent species, any additional time spent in State 3 will not increase the magnitude of the measured voltage. It is to be noted that in the exemplary case depicted by FIG. 5A, the built-in delay is generated by the Schmitt-trigger inverter (IC1B) placed between the activation elements (IC1A) of LED1 and (Q1) of D1. A person skilled in the art will know of alternative delay implementation techniques, such as adding gates, using gates of various technologies (slower, faster), inserting RC filters in-between gates to add delay or simply using "long" traces/wires instead of gates where shorter delays are required.

For many fluorescent species, the lifetime is short enough (in the order of nanoseconds) that the voltage across capacitor C1 may not be measurable. Thus, States 2 and 3 may be performed repeatedly to increase the output voltage level by first going into State 4. In State 4, the detection circuitry is disabled (thus no current present to further charge capacitor C1) before going into State 2 and enabling the excitation light source again. This is done to ensure that the detection circuitry is disabled and that no photocurrent due to light directly from the excitation light source accumulates in the integration capacitor (C1), which could be the case if State 2 were immediately switched to.

In view of the above description, it should become apparent to the skilled person that only the transitions between the states should be fast; the amount of time spent in each state in some cases is actually preferably slower. Common low cost logic ICs can provide such high speed transitions. A 74ALS series Schmitt-trigger inverter (IC1A) drives the emitter light source (LED1, a light-emitting diode). The Schmitt-trigger action means that any circuitry driving inverter IC1A need not be high speed. Because IC1A is a 74ALS series IC, it is capable of switching LED1 in several nanoseconds, permitting detection of the fluorescent species with nanosecond-scale decay times. IC1B drives a MOSFET transistor (Q1) which short-circuits the detector (D1), a photodiode, shunting any unwanted signal (e.g. current) from the circuitry ahead (e.g. integrator module) while the excitation LED is on. In this particular example, IC1B acts as an inverter, ensuring that the detection circuit is off while the excitation circuit is on. However, more generally, it also acts as a very low cost delay line, adding some extra time between the time when the excitation light source is turned off and the time when the detection circuitry is enabled. This is useful, as the light emitted from the excitation source may not instantaneously turn off and because it takes a nonzero amount of time for light from the excitation source to reach the photodiode. The delay line prevents any of the unwanted signal from the excitation light source from reaching the rest of the detection circuitry. As previously noted, shorter delays may be implemented using design techniques familiar to the skilled person. IC3A provides similar functionality to IC1A (removing a need for high speed circuitry outside of this), and implements State 4 of the circuit, as noted above.

In order to remove the need for the rest of the amplification and analog processing circuitry to deal with high frequency signals (which can very quickly become quite expensive and complex), the signal from photodiode D1 is immediately routed through a high speed diode D2 into integration capacitor C1. When Q1, a high speed MOSFET, is turned off, photocurrent (proportional to the intensity of the decaying light emitted by the fluorescent species) is routed through D2 and charges C1. The voltage across C1 is thus proportional to the total amount of light emitted by the fluorescent species over time. Diode D2 allows capacitor C1 to maintain charge even when the preceding circuitry changes state (i.e. the excitation LED turns on again and the photodiode detection circuit turns off), by blocking any current flow into the preceding circuitry. Thus, it is possible to cycle through States 2-4 many times until a sufficient voltage level is obtained across the integration capacitor (C1). The voltage across C1, which will be stable in any state where the detection circuitry is off, may be amplified, processed, and read using low frequency, low cost circuitry (in this example represented by amplifier IC2A).

Figure 5C:
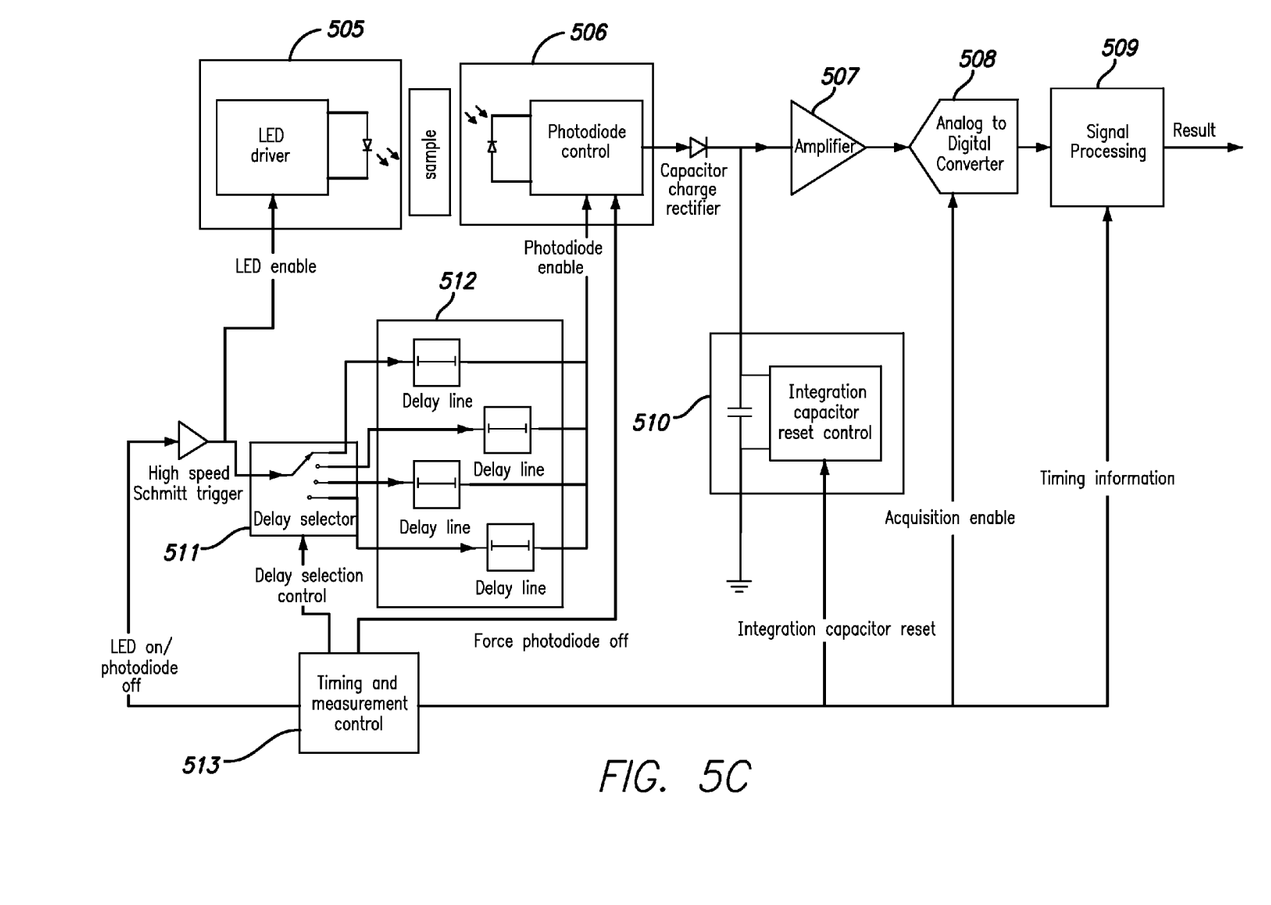
FIG. 5C shows an exemplary block diagram adapted to detect more than one fluorophore that may be too fast for common data acquisition circuits.

The exemplary circuit of FIG. 5A can be used to perform single fluorescent species detection as well as multiplex detection when the lifetime of the multiple species being quantified are distinct enough to be detected by the circuit. FIG. 5C shows a block diagram of a similar embodiment which incorporates several delay lines to be used in connection with additional fluorophores that may be too fast for common data acquisition circuits. FIG. 5C is similar to FIG. 5B, showing the addition of several delay lines (512) corresponding to a particular fluorophore in a sample along with a delay selector switch (511) capable of high frequency signal transfer (the switching itself need not be fast). There are a variety of methods to implement such switching known to those skilled in the art. The timing/measurement controller (513) can select a particular delay line to measure only a single fluorophore. In one embodiment, the shortest delay time will measure a summed signal of all of the fluorophores in the sample. Utilizing the next delay time should result in a signal which excludes the fastest fluorophore, as the detection enable signal is not received until the first fluorophore has stopped emitting any significant amount of light. Utilizing any subsequent slower delay time would then result in a signal that excludes all faster fluorophores. Fluorophores which decay slower than the amplification (507), analog-to-digital converter (508), and signal processing circuitry (509) may be measured directly and do not require a delay line to measure. The selection of fluorophores, number of delay lines to use, maximum speed of the amplifier, ADC, and signal processing circuitry is a compromise that depends on the particular application which a person skilled in the art is capable of determining. Utilizing a selection of delays and measured time dependent data, the signal processing circuit can generate a result corresponding to the concentration or presence of fluorophores within the solution using curve fitting and other methods.

Figure 6:
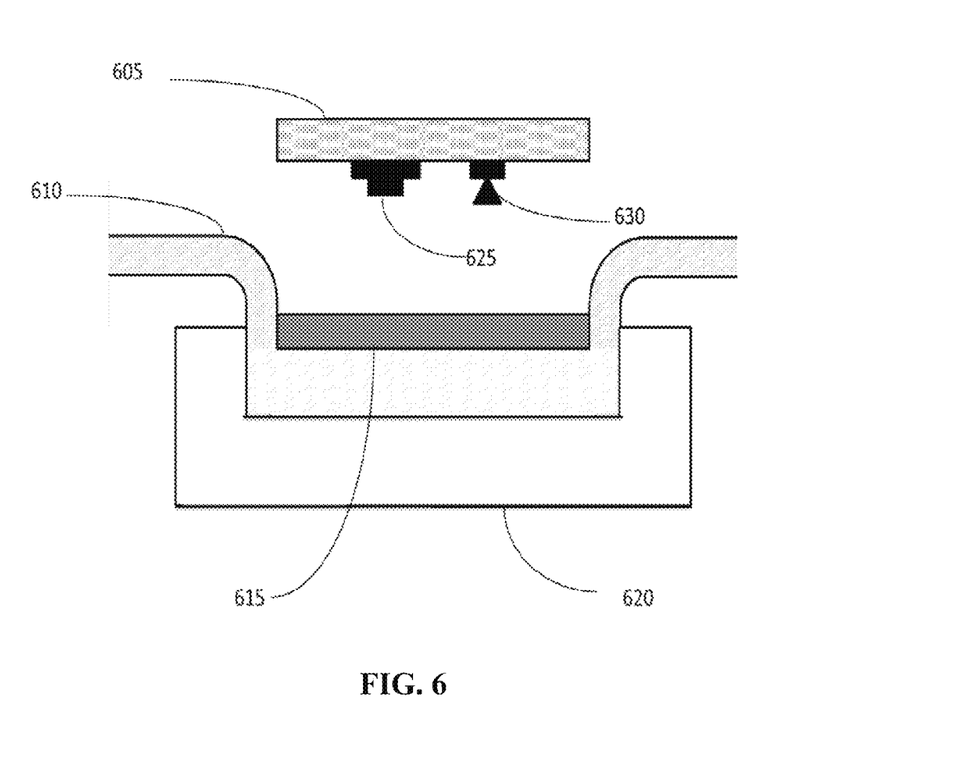
FIG. 6 shows an exemplary embodiment of a microfluidic PCR system using a filterless time-domain multiplex detector.
Figure 7:
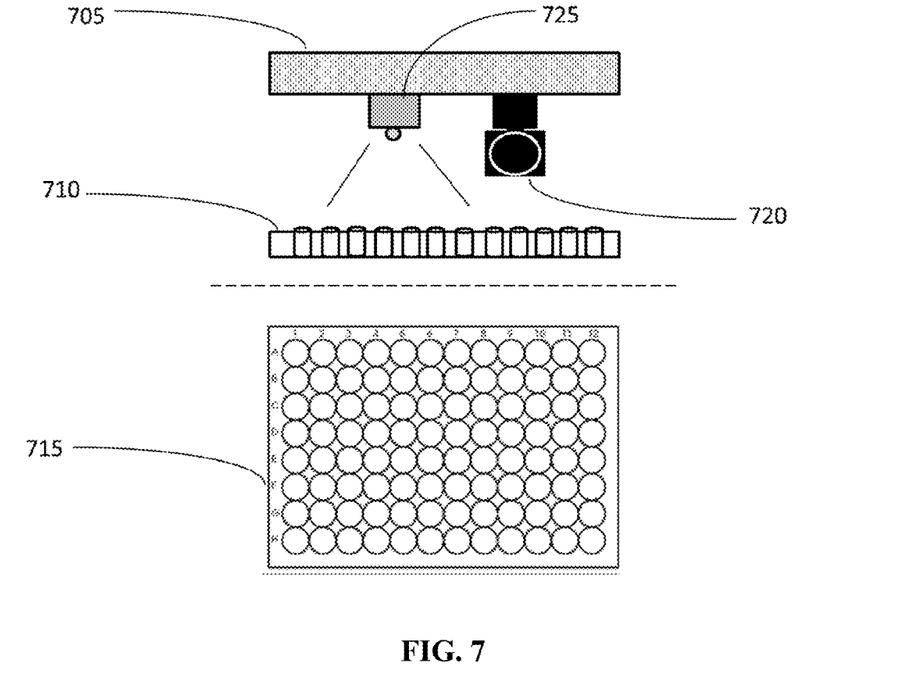
FIG. 7 shows an exemplary embodiment using a filterless time-domain multiplex detector with samples in a multi-well chamber.

In some embodiments, the detection circuit is used in connection with fluorophores labeled to molecules and compounds within a single sample (FIG. 6). In this exemplary embodiment of a microfluidic PCR (polymerase chain reaction) system, an optical system comprising an excitation LED (625) and photodiode (630) face a sample PCR chamber (615). The optical system is connected to a circuit board (605), comprising the optical control, integrator, and output stage. Below, a sample chamber (615) is supported by an apparatus support (620). In the embodiment shown, microfluidic connectors (610) are connected to the sample PCR chamber. FIG. 7 shows a similar embodiment in connection with multiple samples, where the sample chamber comprises multiple wells. In this embodiment, a circuit board (705) is connected to an excitation LED (725) as an exemplary light source and a charge coupled device (CCD) or complementary metal oxide semiconductor (CMOS) image sensor (720) as an exemplary photodetector. A top-down view of the multi-well sample chamber is shown as well (715).

The detection circuit described can be used in many existing applications that use fluorescent species or fluorophores. In some embodiments, the detection circuit is used for laboratory or medical diagnostic purposes. In other embodiments, the detection circuit is used in connection with different fluorophores labeled to different molecules and compounds within a sample or samples. In one embodiment, the detection circuit is used to quantify the fluorescently labeled molecule or compound. In one embodiment, the detection circuit is used in connection with qPCR (quantitative real time polymerase chain reactions), RT-PCR (real-time polymerase chain reactions), or to calculate the rate of gene expression. In another embodiment, the detection circuit is used to determine the rate of protein synthesis. In another embodiment, the detection circuit is used in connection with sequencing reactions of DNA, RNA, or proteins. In another embodiment, the detection circuit is used in connection with FRET (Fluorescence resonance energy transfer) of two or more fluorophores. In another embodiment, the detection circuit is used in connection with FACS (Fluorescence-activated cell sorting) analysis or counting cell numbers. In another embodiment, the detection circuit is coupled to a microscope. In a further embodiment, the detection circuit is used in connection with live cell imaging. In a similar embodiment, the detection circuit is used to calculate the density of fluorophore localization in a cell. In another embodiment, the detection circuit is used to calculate rate of cell motility or movement of intracellular components. In other embodiments, the detection circuit is used in connection with enzyme or viability assays.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by preferred embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible sub-combinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations which is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

The invention claimed is:
1. A filterless detection system for fluorescent chemical species, comprising
a light emitting device (LED) configured to emit light at a wavelength in correspondence of an excitation wavelength of a fluorescent chemical species;

a photodetector (PD) configured to detect light at a wavelength in correspondence of an emission wavelength of the fluorescent chemical species;

a control circuit configured to enable or disable the LED and the PD independently of each other;

a signal processing circuit, operatively connected with the PD and configured to generate time varying signals as a function of the output of the PD, the time varying signals being indicative of the fluorescent chemical species; and a sample chamber comprising an array of detection wells, wherein the filterless detection system is devoid of any optical filter elements.

2. The detection system of claim 1, wherein the control circuit further comprises:

a controlled time delay device to control a time delay between enabling of the LED and disabling of the PD, or between disabling of the LED and enabling of the PD.

3. The detection system of claim 2, wherein the controlled time delay device comprises one or more of: a) one or more transistors, b) one or more transistors with one or more delaying capacitors, and c) wires with controlled trace length.

4. The detection system of claim 2, wherein the control circuit comprises a transistor to control the LED.

5. The detection system of claim 2, wherein the control circuit comprises transistors and a transistor to control the PD.

6. The detection system of claim 2 further comprising a shunting circuitry configured to shunt away from the signal processing circuit a photocurrent generated by the PD in response to a detected light emitted by the fluorescent chemical species.

7. The detection system of claim 6 wherein the shunting circuitry comprises one or more transistors.

8. The detection system of claim 1 further comprising a shunting circuitry configured to shunt away from the signal processing circuit a photocurrent generated by the PD in response to a detected light emitted by the fluorescent chemical species.

9. The detection system of claim 1, wherein a controlled detection is performed in the absence of light emitted from the LED.

10. The detection system of claim 9, wherein during the controlled detection, the signal processing circuit is configured to generate a first voltage proportional to a photocurrent generated by the PD in response to a detected light emitted by the fluorescent chemical species and add the first voltage to a second voltage stored within the signal processing circuit.

11. The detection system of claim 10, wherein the second voltage is in correspondence of photocurrent generated during one or more controlled detection cycles.

12. The detection system of claim 11, wherein the signal processing circuit further comprises a reset circuitry to zero a value of the second voltage.

13. The detection system of claim 11, wherein the signal processing circuit comprises a diode, wherein the diode is in a series connection with a capacitor is used to generate the first voltage and store the second voltage.

14. The detection system of claim 13, wherein the reset circuitry comprises a transistor operatively coupled to terminals of the capacitor and configured to discharge the capacitor when activated.

15. The detection system of claim 10, wherein the signal processing circuit comprises an integrator.

16. The detection system of claim 1, further comprising a microfluidic connector connected to the sample chamber.

17. The detection system of claim 1, wherein the detection system is used in medical or laboratory diagnostic detection.

18. The detection system of claim 1, wherein the detection system is used in qPCR, in RT-PCR, sequencing reactions, FRET, FACS, cell imaging, or to quantify the fluorescently labeled molecule.

* * * * *